US011520069B2

(12) United States Patent
Jones et al.

(10) Patent No.: US 11,520,069 B2
(45) Date of Patent: Dec. 6, 2022

(54) FOOTWEAR SCANNING SYSTEMS AND METHODS

(71) Applicant: Battelle Memorial Institute, Richland, WA (US)

(72) Inventors: A. Mark Jones, West Richland, WA (US); David M. Sheen, Richland, WA (US); Stanley L. Owsley, Jr., Pasco, WA (US)

(73) Assignee: Battelle Memorial Institute, Richland, WA (US)

( * ) Notice: Subject to any disclaimer, the term of this patent is extended or adjusted under 35 U.S.C. 154(b) by 217 days.

(21) Appl. No.: 16/894,484

(22) Filed: Jun. 5, 2020

(65) Prior Publication Data
US 2021/0325560 A1 Oct. 21, 2021

Related U.S. Application Data

(60) Provisional application No. 63/012,622, filed on Apr. 20, 2020.

(51) Int. Cl.
*G01R 27/04* (2006.01)
*G01R 27/32* (2006.01)
(Continued)

(52) U.S. Cl.
CPC ........... *G01V 3/12* (2013.01); *G01N 22/00* (2013.01); *G01N 22/02* (2013.01); *G01N 22/04* (2013.01);
(Continued)

(58) Field of Classification Search
CPC .......... G01V 3/12; G01V 8/005; G01N 22/00; G01N 22/04; G01N 22/02; G01N 33/2823;
(Continued)

(56) References Cited

U.S. PATENT DOCUMENTS

| 5,408,244 A | 4/1995 | Mackenzie |
| 5,455,590 A | 10/1995 | Collins et al. |

(Continued)

FOREIGN PATENT DOCUMENTS

| AU | 2014257481 | 4/2017 |
| CN | 102508205 | 7/2013 |

(Continued)

OTHER PUBLICATIONS

Fumeaux, "Finite-Volume Time-Domain Analysis of a Cavity-Backed Archimediean Spiral Antenna", IEEE Transactions on Antennas and Propagation, 2006, 54(3), United States, pp. 844-851.

(Continued)

*Primary Examiner* — Raul J Rios Russo
(74) *Attorney, Agent, or Firm* — Wells St. John P.S.

(57) ABSTRACT

Footwear scanning systems and associated methods are described. According to one aspect, a footwear scanning system includes a base, a shuttle configured to rotate beneath the base, wherein the shuttle comprises an antenna array configured to transmit electromagnetic waves through the base into footwear above the base during the rotation of the shuttle and to receive electromagnetic waves reflected from the footwear during the rotation of the shuttle, a transceiver coupled with the antenna array and configured to apply electrical signals to the antenna array to generate the transmitted electromagnetic waves and to receive electrical signals from the antenna array corresponding to the received electromagnetic waves, and processing circuitry configured to process an output of the transceiver corresponding to the received electromagnetic waves to provide information regarding contents within the footwear.

31 Claims, 10 Drawing Sheets

(51) Int. Cl.
| | | |
|---|---|---|
| *G01V 3/12* | (2006.01) | |
| *G01N 22/00* | (2006.01) | |
| *H04B 1/38* | (2015.01) | |
| *G01N 22/04* | (2006.01) | |
| *G01N 22/02* | (2006.01) | |
| *G01N 33/28* | (2006.01) | |
| *G01N 33/46* | (2006.01) | |
| *G01N 17/00* | (2006.01) | |

(52) U.S. Cl.
 CPC .......... *G01N 33/2823* (2013.01); *H04B 1/38* (2013.01); *G01N 17/00* (2013.01); *G01N 33/46* (2013.01)

(58) Field of Classification Search
 CPC .......... G01N 33/46; G01N 17/00; H04B 1/38; A43D 1/08; G01S 7/41; G01S 13/426; G01S 13/887; G01S 13/08
 USPC ... 324/76.11–76.83, 459, 600, 629, 637, 642
 See application file for complete search history.

(56) References Cited

U.S. PATENT DOCUMENTS

| | | | |
|---|---|---|---|
| 5,557,283 | A | 9/1996 | Sheen et al. |
| 6,970,087 | B2 | 11/2005 | Stis |
| 7,034,746 | B1 | 4/2006 | McMakin |
| 7,106,058 | B2 | 9/2006 | Wilker et al. |
| 7,253,766 | B2 | 8/2007 | Foote et al. |
| 7,292,033 | B2 | 11/2007 | Pusiol |
| 7,295,146 | B2 | 11/2007 | McMakin et al. |
| 7,327,137 | B1 | 2/2008 | Crowley et al. |
| 7,365,672 | B2 | 4/2008 | Keller et al. |
| 7,397,239 | B1 | 7/2008 | Crowley et al. |
| 7,405,692 | B2 | 7/2008 | McMakin et al. |
| 7,511,514 | B2 | 3/2009 | Crowley et al. |
| 7,548,185 | B2 | 6/2009 | Sheen |
| 7,595,638 | B2 | 9/2009 | Crowiey |
| 7,750,631 | B2 | 7/2010 | Crowley |
| 7,763,868 | B2 | 7/2010 | Ouchi et al. |
| 7,804,442 | B2 | 9/2010 | Ammar |
| 7,868,758 | B2 | 1/2011 | Barral et al. |
| 7,986,260 | B2 | 7/2011 | McMakin et al. |
| 8,278,921 | B2 | 10/2012 | Crowley |
| 8,487,820 | B2 | 7/2013 | Tajima |
| 8,525,515 | B2 | 9/2013 | Itozaki |
| 8,531,915 | B2 | 9/2013 | Ammar |
| 8,654,922 | B2 | 2/2014 | Brendahan |
| 8,937,570 | B2 | 1/2015 | Sheen |
| 9,024,804 | B2 | 5/2015 | Shi |
| 9,715,012 | B2 | 7/2017 | Fernandes |
| 2004/0222790 | A1 | 11/2004 | Karmi et al. |
| 2005/0073307 | A1 | 4/2005 | Manneschi |
| 2005/0116825 | A1 | 6/2005 | Manneschi |
| 2005/0232487 | A1 | 10/2005 | Fleisher |
| 2006/0104480 | A1 | 5/2006 | Fleisher |
| 2007/0073492 | A1 | 3/2007 | Manneschi |
| 2007/0158571 | A1 | 7/2007 | Cote et al. |
| 2007/0211922 | A1 | 9/2007 | Crowley et al. |
| 2007/0263907 | A1 | 11/2007 | McMakin |
| 2008/0164420 | A1 | 7/2008 | Manneschi |
| 2009/0058710 | A1 | 3/2009 | Levitan |
| 2009/0314943 | A1 | 12/2009 | Breit et al. |
| 2009/0322866 | A1 | 12/2009 | Stotz |
| 2010/0123571 | A1 | 5/2010 | Crowley et al. |
| 2010/0213365 | A1 | 8/2010 | Crowley et al. |
| 2011/0129063 | A1 | 6/2011 | Bendahan |
| 2011/0163876 | A1 | 7/2011 | Uemura et al. |
| 2012/0069963 | A1 | 3/2012 | Song |
| 2012/0105267 | A1 | 5/2012 | DeLia et al. |
| 2012/0307967 | A1 | 12/2012 | Smith |
| 2014/0091965 | A1 | 4/2014 | Sheen |
| 2014/0182370 | A1 | 7/2014 | Kienzle |
| 2014/0320331 | A1* | 10/2014 | Fernandes ............ G01S 13/887 342/22 |
| 2015/0066712 | A1* | 3/2015 | Altieri ................ G06Q 10/087 705/28 |
| 2015/0369756 | A1 | 12/2015 | Rezgiu et al. |
| 2016/0000188 | A1* | 1/2016 | Hanft ...................... A43B 7/28 700/98 |

FOREIGN PATENT DOCUMENTS

| | | |
|---|---|---|
| DE | 10 2010 014795 | 7/2011 |
| EP | 2 302 413 | 3/2011 |
| WO | PCT/US2014/031501 | 12/2014 |
| WO | PCT/US2014/031501 | 10/2015 |
| WO | PCT/US2021/027232 | 8/2021 |

OTHER PUBLICATIONS

Keller et al., "Privacy Algorithm for Airport Passenger Screening Portal", Proceedings of SPIE 4055, Applications and Science of Computational Intelligence III 476, Mar. 30, 2000. United States, pp. 476-483.

McMakin et al., "Biometric Identification using Holographic Radar Imaging Techniques", Proceedings of SPIE 6538, Sensors, and Command, Control, Communications, and intelligence (C3I) Technologies for Homeland Security and Homeland Defense VI 65380C, Apr. 27, 2007, United States, 12 pages.

McMakin et al., "Dual-Surface Dielectric Depth Detector for Holographic Millimeter-Wave Security Scanners", Proceedings of SPIE 7309, Passive Millimeter-Wave Imaging Technology XII 73090G, May 1, 2009, United States, 10 pages.

McMakin et al., "Holographic Radar Imaging Privacy Techniques Utilizing Dual-Frequency Implementation", Proceedings of SPIE 6943, Sensors, and Command, Control, Communications, and Intelligence (C3I) Technologies for Homeland Security and Homeland Defense VII 69430P, Apr. 3, 2008, United States 10 pages.

Mensa, D., "High Resolution Radar Cross-Section imaging", Norwood, MA, Artech House, 1991, 10 pages.

Sheen et al., "Combined Illumination Cylindrical Millimeter-Wave Imaging Technique for Concealed Weapon Detection", Proceedings of SPIE, 2000, 4032, United States, pp. 52-60.

Soumekh, "A System Model and inversion for Synthetic Aperture Radar Imaging", IEEE Transactions on Image Processing, 1992, 1(1), United States, pp. 64-76.

VolumeRover, Computational Visualization Center, Printed from the Internet Apr. 3, 2013, http:/www.cs.utexas.edu/~bajaj/cvcwp/?page_id=100, 3 pages.

Ahmed et al., "A Novel Fully Electronic Active Real-Time Imager Based on a Planar Multistatic Sparse Array", IEEE Transactions on Microwave Theory and Techniques vol. 59, No. 12, Dec. 2011, United States, pp. 3567-3576.

Fernandes et al. "Three-Dimensional Millimeter-Wave Imaging for Concealed Threat Detection in Shoes", SPIE Defense, Security, and Sensing Proceedings vol. 8715, Baltimore, Maryland, 2013, United States, 8 pages.

Fernandes et al., U.S. Appl. No. 15/658,111, filed Jul. 24, 2017, titled "Footwear Scanning Systems and Methods", 41 pages.

Jones et al., "Wideband Archimedean Spiral Antenna for Millimeter-Wave Imaging Array", IEEE International Symposium on Antennas and Propagation USNC/URSI National Radio Science Meeting, 2017, United States, pp. 845-846.

Sheen et al., "Three-Dimensional Millimeter-Wave Imaging for Concealed Weapon Detection", IEEE Transactions on Microwave Theory and Techniques vol. 49, No. 9, Sep. 2001, United States, pp. 1581-1592.

Sheen et al., "Near-Field Three-Dimensional Radar Imaging Techniques and Applications", Applied Optics vol. 49, No. 19, Jul. 2010, United States, pp. E83-E93.

Sheen et al., "Wide-Bandwidth, Wide-Beamwidth, High-Resolution, Millimeter-Wave Imaging for Concealed Weapon Detection", SPIE Defense, Security, and Sensing Proceedings vol. 8715, Baltimore, Maryland, 2013, United States, 11 pages.

Sheen et al., U.S. Appl. No. 63/012,622, filed Apr. 20, 2020, titled "Footwear Scanning Systems and Associated Methods", 43 pages.

(56) References Cited

OTHER PUBLICATIONS

Sheen, "Sparse Multi-Static Arrays for Near-Field Millimeter-Wave Imaging", IEEE Global Conference on Signal and Information Processing (GlobalSIP), Dec. 2013, United States, pp. 699-702.
Busch, "Recycling Program Adds to Rubber Flooring's Environmental Advantages", available online at https://lands.design/articles/41001/recydling-program-adds-rubber-floorings-environmental-advantages, Jul. 9, 2010, 11 pages.
Osmun, "What We Didn't Know About Dielectric Properties of Plastics", available online at https://www.ptonline.com/articles/what-we-didn't-know-about-dielectric-properties-of-plastics, May 1, 2004, 4 pages.

* cited by examiner

FOOTWEAR SCANNING SYSTEMS AND METHODS

RELATED PATENT DATA

This application claims the benefit of U.S. Provisional Patent Application Ser. No. 63/012,622, filed Apr. 20, 2020, titled "Footwear Scanning Systems and Associated Methods", the disclosure of which is incorporated herein by reference.

STATEMENT AS TO RIGHTS TO INVENTIONS MADE UNDER FEDERALLY-SPONSORED RESEARCH AND DEVELOPMENT

This invention was made with Government support under Contract DE-AC05-76RL01830 awarded by the U.S. Department of Energy. The Government has certain rights in the invention.

TECHNICAL FIELD

This disclosure relates to footwear scanning systems and methods.

BACKGROUND OF THE DISCLOSURE

Screening of personnel for concealed weapons has become increasingly important as threats to aviation and other high-security venues have evolved. The security posture at airports has been driven by high-profile events. Initial security focus was directed to detecting concealed handguns and knives. Metal detectors for passenger screening and x-ray systems for hand-carried baggage and items were largely enough to mitigate threats.

Current screening methods generally rely upon dual-energy transmission or computed-tomography (CT) x-ray technology for baggage and hand-carried items and metal detectors or millimeter-wave scanners for passenger screening. For this technology to operate effectively, passengers often divest outer layers of clothing as well as belts, hats, and shoes. Clothing divestment, especially shoes, significantly slows the screening process, checkpoint throughput and is inconvenient for passengers.

Comprehensive screening of shoes is an important component of the aviation security screening process as individuals have modified shoes to conceal explosives. Divestment of shoes is typically required because most imaging systems do not adequately scan footwear, particularly the soles of the shoes, which can be quite substantial in some styles of footwear.

At least some of the aspects of the disclosure are directed to footwear scanning system and associated methods.

BRIEF DESCRIPTION OF THE DRAWINGS

Example embodiments of the disclosure are described below with reference to the following accompanying drawings.

DETAILED DESCRIPTION OF THE DISCLOSURE

This disclosure is submitted in furtherance of the constitutional purposes of the U.S. Patent Laws "to promote the progress of science and useful arts" (Article 1, Section 8).

Example embodiments of footwear scanning systems are described below. Some embodiments described below enable footwear of people to be scanned for metallic and non-metallic threats without divestment of their footwear thereby increasing screening throughput and convenience to people being screened.

Some embodiments implement mm-wave imaging utilizing millimeter-waves that are typically defined as electromagnetic waves in the 30-300 GHz range which have wavelengths ranging from 1 mm to 10 mm. This range may be extended to include frequencies in the microwave range down to 10 GHz. Waves in the 10-100 GHz range are highly effective for security screening since these waves can penetrate dielectric materials including plastics, ceramics, wood, clothing, leather, and many other materials. The waves pass through these materials with modest attenuation and reflect off the body and any concealed objects. Active, wide-aperture, near-field imaging systems can achieve spatial resolution on the order of one-half wavelength. Wide-bandwidth also allows fine depth-resolution, so mm-wave imaging systems can be designed for fully 3D high-resolution imaging performance.

Accurately imaging the soles of footwear using mm-waves involves overcoming several challenges. The scanner and footwear represent a heterogeneous medium of different layers with different dielectric constants that introduces several undesired effects including stray scattering, defocusing, multipath, and attenuation. These characteristics vary with frequency. Low frequencies have longer wavelengths which can penetrate better and are less affected by defocusing. High frequencies provide higher resolution if the medium supports it, but are more likely to be defocused.

Operation over an extremely wide frequency range such as 10 to 40 GHz provides an ability to optimize performance trade-offs of penetration, resolution, and image quality. Extremely wide bandwidth also improves depth resolution, allowing components of the shoes and potential threats to be spatially isolated in the 3D images. Wide antenna beamwidth enhances spatial resolution and may provide some geometrical averaging that reduces the effects of material inhomogeneity (including defocusing and multipath). In some embodiments discussed below, images of concealed contents of the footwear are reconstructed from the radar data using round-trip phase shifts of the electromagnetic waves through different materials having different dielectric constants.

Figure 1:
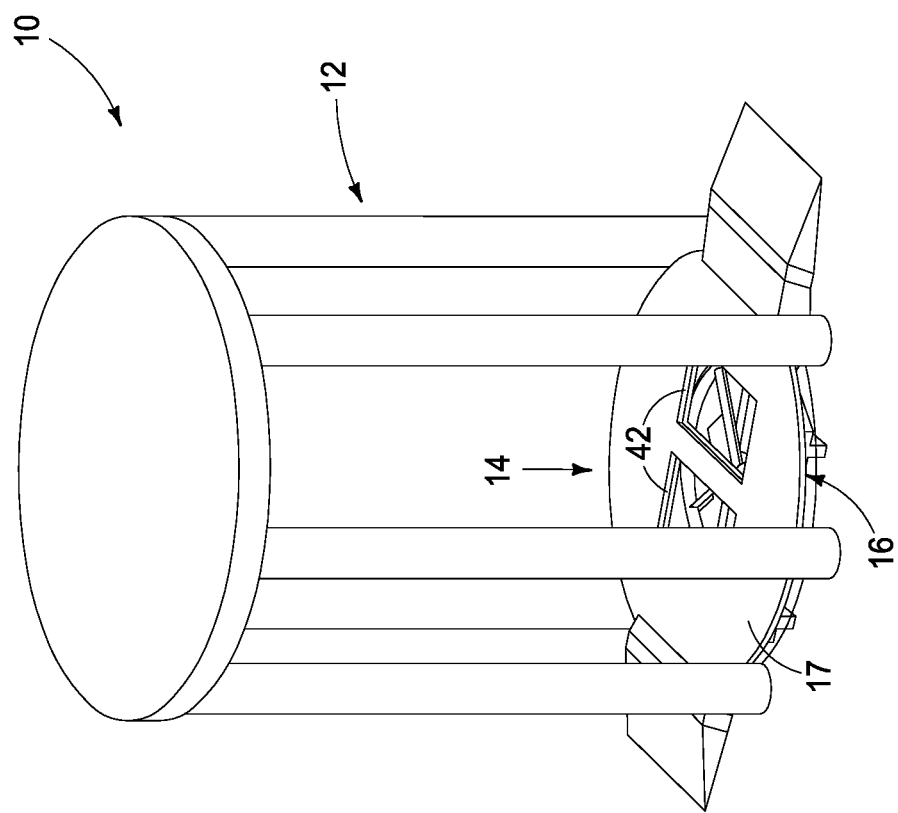
FIG. 1 is an isometric view of a personnel scanning apparatus according to one embodiment.

Referring to FIG. 1, a personnel scanning apparatus 10 is shown according to one embodiment. The illustrated apparatus 10 includes a body scanning system 12 and a footwear scanning system 14. This footwear scanning system 14 includes a low-profile scanning base 16 that supports the person wearing their footwear above one or more scanned linear mm-wave antenna arrays as discussed further below. In some embodiments, the footwear scanning system 14 has a height of approximately 10 cm or less for straightforward implementation into personnel scanning apparatus 10. A commercial implementation of the footwear scanning system 14 may include all electronics and integrate the system 14 into the complementary body scanning system 12.

During operation, a person enters into the apparatus 10, stands upon a base 16, and body and footwear scanning systems 12, 14 include respective antenna arrays that emit and receive electromagnetic energy that is used to generate radar data that can reveal contents, such as threats, within clothing and footwear of the person. The systems 12, 14 are used to detect both metallic and non-metallic threats, such as firearms and concealed explosives, in some embodiments. In example embodiments discussed further below, the antennas of scanning systems 12, 14 move with respect to the person who maintains a stationary position while wearing their footwear during the scanning operations.

The depicted base 16 includes a plurality of window interfaces 42 that are configured to pass electromagnetic waves between the antennas and the footwear. During scanning, the person stands with one foot and the footwear thereon upon each of the window interfaces 42 that are configured to support the weight of the person during scanning.

Base 16 also includes a platform 17 about the window interfaces 42 and platform 17 is configured to block electromagnetic waves in one embodiment. Upper surfaces of the window interfaces 42 and an upper surface of platform 17 are provided at the same height in one implementation providing a continuous flush surface for people entering and leaving the system 10.

Figure 2:
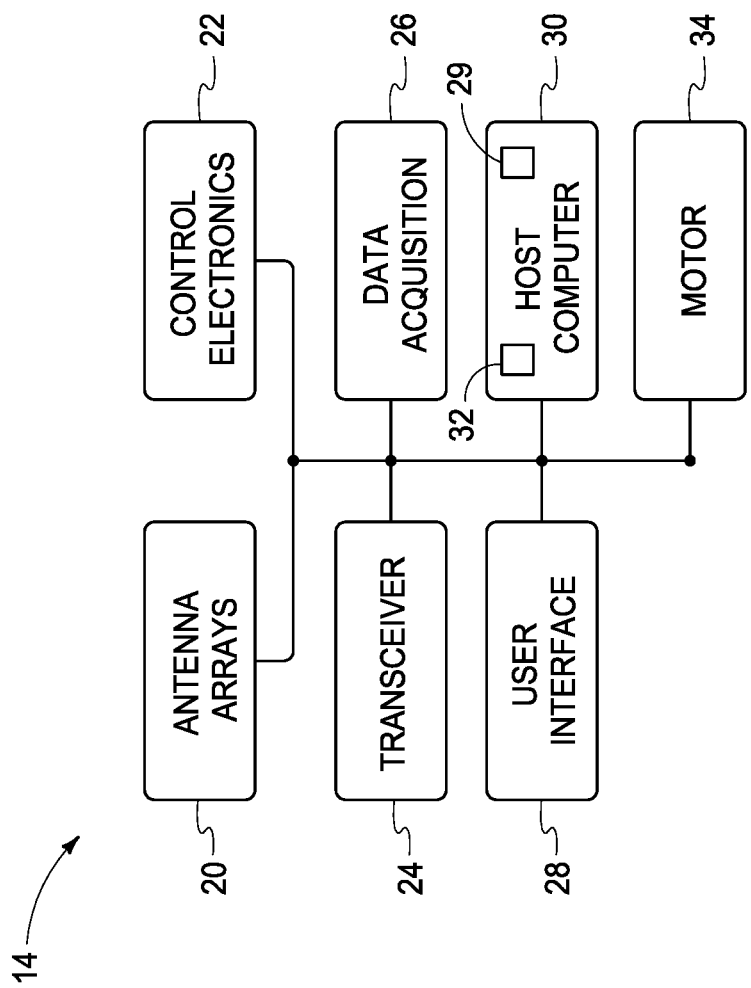
FIG. 2 is a functional block diagram of components of a personnel scanning apparatus according to one embodiment.

Referring to FIG. 2, components of a footwear scanning system 14 are shown according to one example embodiment. The illustrated footwear scanning system 14 includes antenna arrays 20, control electronics 22, a transceiver 24, a data acquisition system 26, a user interface 28, a host computer 30, and a motor 34. Additional arrangements of system 14 are possible including more, less and/or alternative components.

Antenna array 20 comprises a plurality of transmit antennas which are configured to emit electromagnetic energy towards footwear worn by a person being scanned. The transmit antennas of antenna array 20 emit the electromagnetic energy responsive to electrical signals received from transceiver 24. Antenna array 20 further comprises a plurality of receive antennas which are configured to receive electromagnetic energy reflected from the footwear and to output electrical signals to the transceiver 24 and which correspond to the received electromagnetic energy. In some embodiments discussed below, plural antenna arrays 20 are moved with respect to the person to scan their footwear.

Figure 5B:
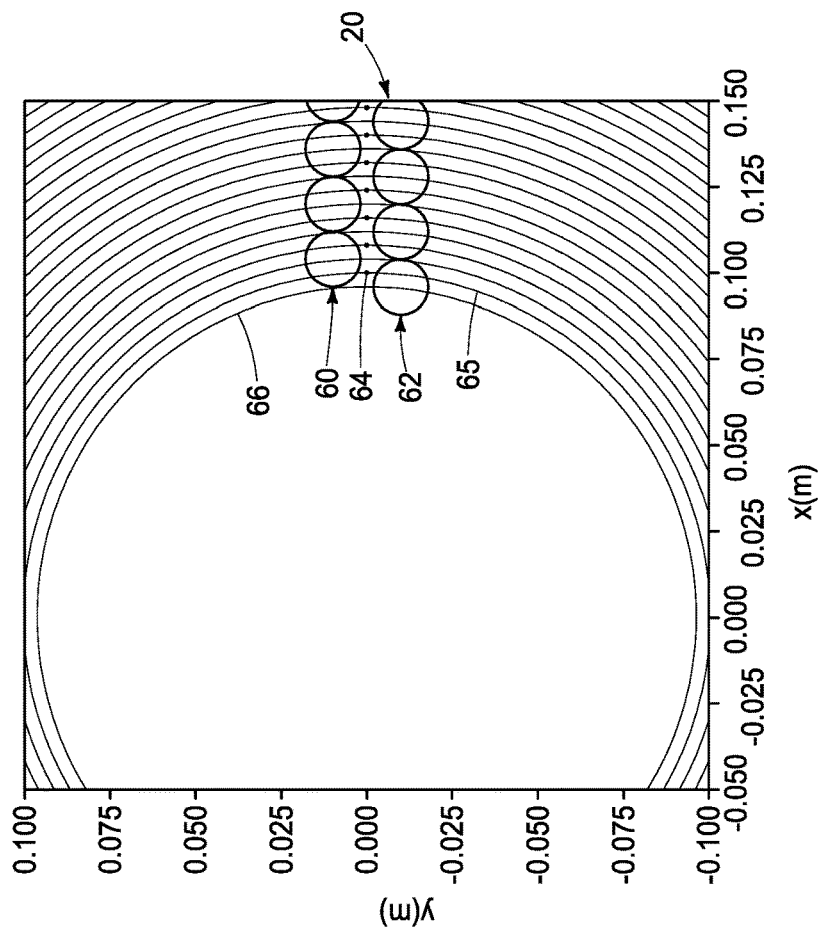
FIGS. 5A and 5B are illustrative representations of scanning operations of a footwear scanning system according to one embodiment.
Figure 5A:
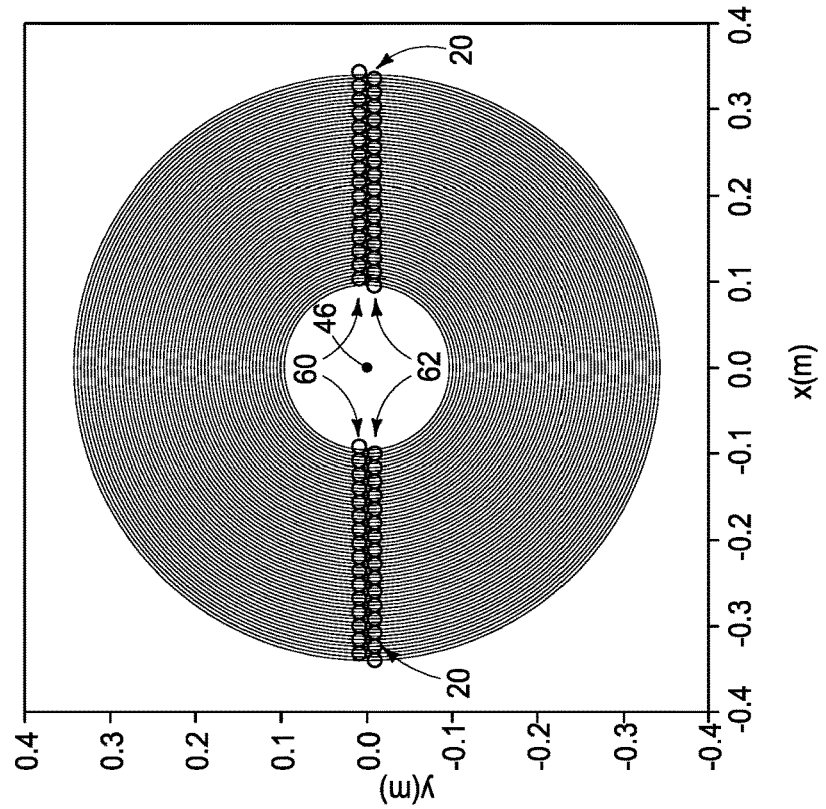

Antenna system 20 may additionally include a switching network or matrix to selectively choose different pairs of transmit and receive antennas in some embodiments. As discussed below, the antenna array 20 may be moved during scanning operations including transmitting and receiving electromagnetic signals. Details regarding example configurations of antenna array(s) 20 are shown in FIGS. 5A and 5B.

Control electronics 22 are configured to control transmit and receive operations of antenna array 20, including switching of antennas therein, as well as operations of transceiver 24 and data acquisition system 26.

Transceiver 24 is coupled with the antenna array 20 and configured to apply electrical signals to the antenna array 20 to generate the transmitted electromagnetic waves and to receive electrical signals from the antenna array 20 corresponding to received electromagnetic waves. Additional details of one implementation of transceiver 24 are discussed below.

The data acquisition system 26 acquires and digitizes the transceiver output data. The data acquisition system 26 also buffers the transceiver output data and sends it to the host computer 30.

User interface 28 includes a computer monitor configured to depict visual images for observation by an operator, for example, scanned images revealing contents hidden within footwear of a person being scanned. User interface 28 is additionally configured to receive and process inputs from an operator. In some embodiments, host computer 30 uses automated threat detection algorithms to inspect the generated imagery for threats.

Host computer 30 includes processing circuitry 29 configured to perform various operations of footwear scanning system 14. In one embodiment, processing circuitry 29 is arranged to process data, control data access and storage, issue commands, and control other desired operations. Processing circuitry 29 may comprise circuitry configured to implement desired programming provided by appropriate computer-readable storage media in at least one embodiment. For example, the processing circuitry 29 may be implemented as one or more processor(s) and/or other structure configured to execute executable instructions including, for example, software and/or firmware instructions. Other exemplary embodiments of processing circuitry 29 include hardware logic, PGA, FPGA, ASIC, state machines, and/or other structures alone or in combination with one or more processor(s). These examples of processing circuitry 29 are for illustration and other configurations are possible.

In one embodiment, processing circuitry 29 performs waveform signal processing and calibration, configures data acquisition, controls scanning electronics, controls the transceiver 24, controls the antenna array 20, processes received radar data and generates information regarding contents within the footwear, for example by generating image data for use in displaying graphical images of the target footwear via the computer monitor of user interface 28. The host computer 30 may be implemented as a high-performance PC workstation that supports fast image reconstruction and processing that exploits parallel processor architecture of modern Windows® computers in one more specific embodiment.

Host computer 30 also includes storage circuitry 32 configured to store programming such as executable code or instructions (e.g., software and/or firmware) used by the host computer, electronic data, databases (e.g., look up tables or LUTs), radar data, image data, or other digital information and may include computer-readable storage media. At least some embodiments or aspects described herein may be implemented using programming stored within one or more computer-readable storage medium of storage circuitry 32 and configured to control appropriate processing circuitry 29 of the host computer 30.

The computer-readable storage medium may be embodied in one or more articles of manufacture which can contain, store, or maintain programming, data and/or digital information for use by or in connection with an instruction execution system including processing circuitry 29 in the exemplary embodiment. For example, exemplary computer-readable storage media may be non-transitory and include any one of physical media such as electronic, magnetic, optical, electromagnetic, infrared or semiconductor media.

Motor 34 is configured to move the antenna array 20 during scanning operations. Movement of the antenna array 20 is rotational in the presently described embodiment.

In one example, motor 34 is implemented as a stepper motor and is configured to provide data indicative of movement and location or position information of the antennas of the antenna array 20 during scanning operations. For example, the motor 34 may provide the data regarding the locations of the antennas to host computer 30 for use in processing of radar data from the antenna array 20 as discussed below.

Figure 3:
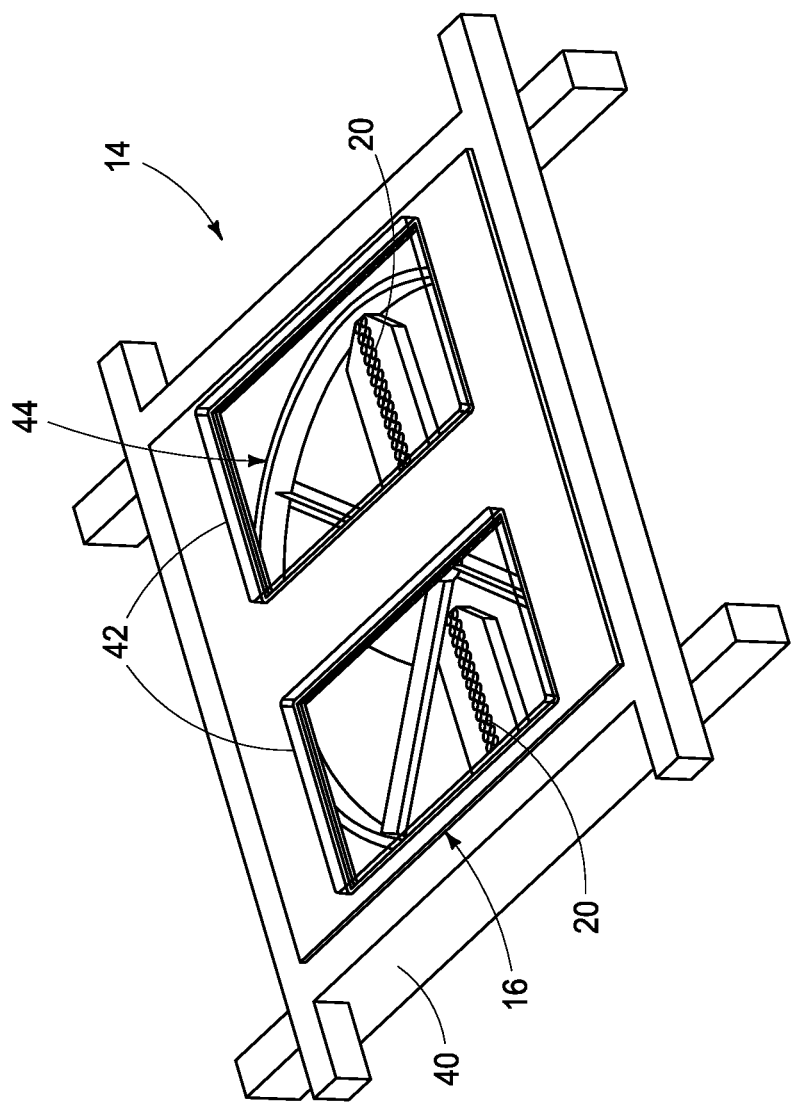
FIG. 3 is an isometric view of a footwear scanning system according to one embodiment.

Referring to FIG. 3, additional details regarding footwear scanning system 14 are shown according to one embodiment and body scanning system 12 of FIG. 1 has been omitted. The illustrated system 14 includes a support structure 40 that supports base 16. As mentioned above, base 16 includes a plurality of footwear interfaces 42 that are each configured to contact and support individual footwear worn by a person being scanned by system 14 (the footwear and platform 17 are not shown in FIG. 3). A plurality of antenna arrays 20 are mounted underneath the base 16 and footwear with their antennas directed upward.

A shuttle 44 is configured to rotate below base 16 during scanning operations and shuttle 44 includes one or more antenna arrays 20 configured to transmit electromagnetic waves through the footwear interfaces 42 of the base 16 into footwear above the base 16 during the rotation of the shuttle 44 and to receive electromagnetic waves reflected from the footwear during the rotation of the shuttle 44. In one embodiment, motor 34 is configured to apply a force to shuttle 44 to rotate the shuttle 44 about an axis and is also configured to provide information regarding movements of shuttle 44 that are indicative of movement and positions of the antenna array 20 at different moments in time during the scanning operations.

Figure 4:
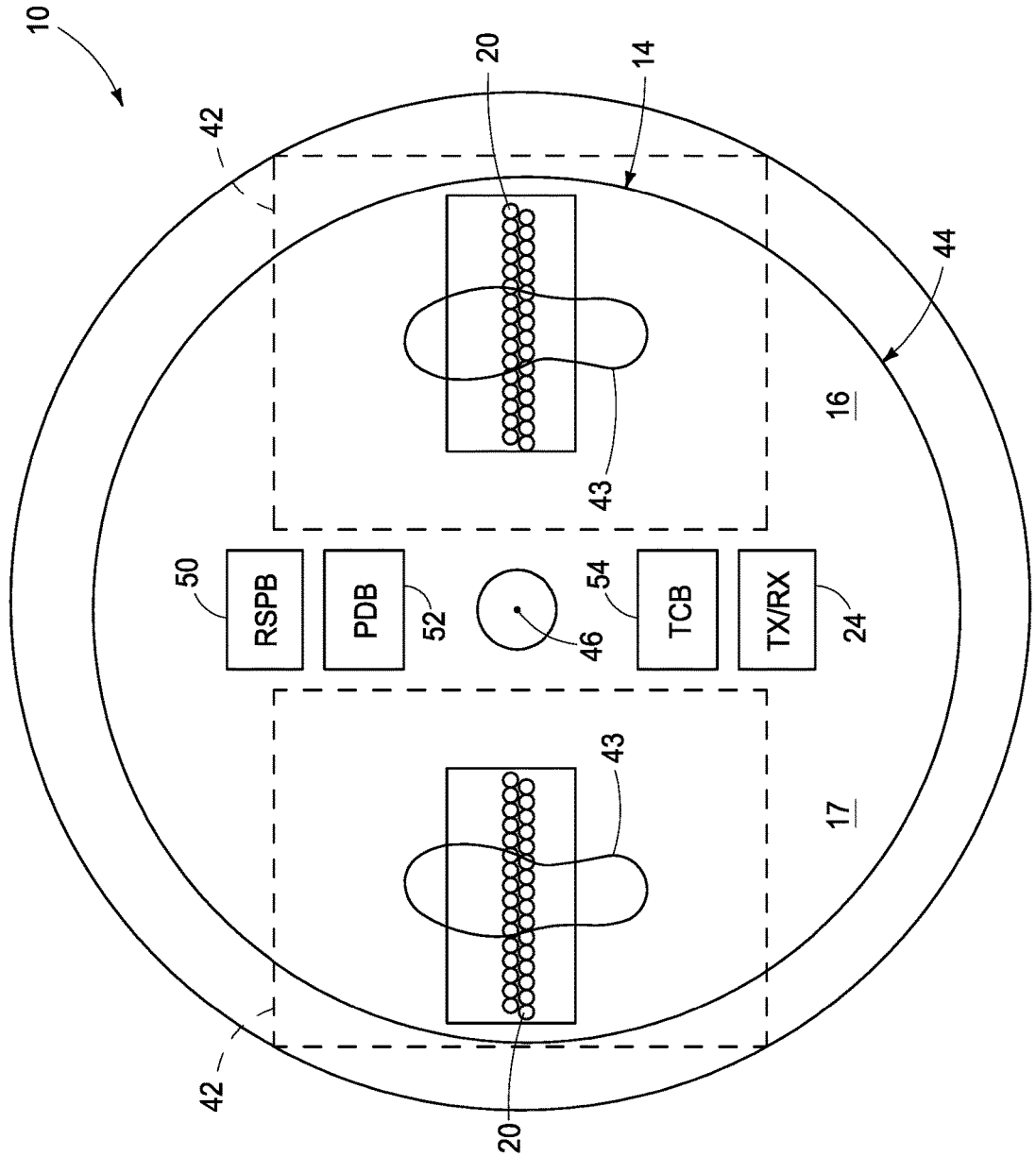
FIG. 4 is a plan view of a footwear scanning system according to one embodiment.

Referring to FIG. 4, the depicted embodiment of footwear scanning system 14 includes two antenna arrays 20 each including two linear columns of antennas including a column of sixteen transmit antennas and a column of sixteen receive antennas and having an antenna spacing of 14-16 mm.

The linear antenna arrays 20 are rotationally scanned below the person and footwear being scanned in the embodiment of FIGS. 3-5. The first and second antenna arrays 20 are configured to transmit and receive electromagnetic waves with respect to the footwear 43 from locations on opposite sides of axis 46 of rotation of the shuttle 44.

Motor 34 discussed above is configured to rotate shuttle 44 about axis 46 beneath the base 16 during scanning operations as the person stands stationary within system 10 and their footwear 43 contacts and is supported by footwear interfaces 42. The antenna arrays 20 are swept below the footwear interfaces 42 and footwear 43 thereon during rotation of the shuttle 44.

Some radar, power and control circuit components of footwear scanning system 14 are also mounted to and supported by shuttle 44. In the embodiment of FIG. 4, a radar sensor processor board (RSPB) 50 is an embedded computer system composed of a processor, field programmable gate array (FPGA), and high-speed two-channel analog-to-digital convertors (ADC). RSPB 50 serves to control the operation of the array 20, implement operations as the data acquisition system including digitizing the signals from the transceiver 24, which then transfers the digitized radar data to host computer 30 for further processing (where the focusing computation is performed in one embodiment).

A power distribution board (PDB) 52 contains a set of DC to DC convertors that allow convenient distribution of a single DC power supply voltage (e.g. 48 V) which is then used to create other DC voltages required by the electronic components, e.g., +/−5V, +/−15 V, etc.

A transceiver control board (TCB) 54 provides electronic control of the transceiver 24 (start and stop of a frequency sweep, etc.) and provides generation, control, and distribution of all of the switch logic lines that determine which array elements of antenna arrays 20 are active at each instant of time.

Transceiver 24 is a heterodyne frequency-modulated continuous wave (FM-CW) design in one embodiment. Transceiver 24 creates a frequency sweep from 10 to 40 GHz, amplifies it and directs it to the selected transmit antenna through a microwave/mm-wave switching network. This signal propagates from the transmit antenna through the layered medium and is scattered by the imaging target (footwear) as well as the layered media interfaces. The scattered signal is received by one of the receive antennas, which is selected by a separate microwave/mm-wave switch network.

The received signal is down-converted by transceiver 24 to an intermediate frequency (IF) using a version of the transmitted sweep that is frequency offset by the intermediate frequency. The received intermediate frequency signal is then down-converted in quadrature to baseband using the reference intermediate frequency. This complex output signal captures the in-phase (I) and quadrature (Q) waveforms that define the scattered phase and amplitude signal $S(a_1, a_2, f)$ used for image reconstruction and is outputted from the transceiver 24 and processed by processing circuitry of the host computer 30 to provide information regarding contents within the footwear 43, such as images of weapons, explosives, etc. within the footwear. The frequency f is proportional to time during the sweep and can be collected using uniform digitization of the received signals. The aperture position $(a_1, a_2)$ is defined by the position of the antenna array 20 and array element selection.

Antenna arrays 20 emit electromagnetic energy that passes through an air gap and footwear interfaces 42, is reflected by contents with the footwear 43, and received by the antenna arrays 20. Footwear interfaces 42 are also referred to as dielectric windows that pass electromagnetic energy emitted from the antenna arrays 20 and reflected by the footwear 43. Footwear interfaces 42 are strong enough to support the weight of the person being scanned and operate to protect the antenna arrays 20. Optimal performance is obtained for footwear interfaces 42 that are transparent to the mm-wave illumination and have low attenuation over the microwave and millimeter-wave frequency bands to not adversely affect imaging performance. In some embodiments, footwear interfaces 42 have uniform propagation properties.

In general, it is desired for the material of the footwear interfaces 42 to have feature sizes that are much smaller than the wavelengths of the electromagnetic energy being used (e.g., down to 8 mm). Plastic materials having lower dielectric constants (e.g., less than 4) may be used since reflections from the footwear interfaces 42 increase with increasing dielectric constant. The footwear interfaces 42 may have a thickness between upper and lower surfaces within a range of 5-50 mm depending on the mechanical strength and stiffness of the interface material, and the amount of deflection that is allowed for the design. It is noted that thicker windows may be useful for separating interface reflections from the desired target reflections, but a low-profile scanner is also desirable for operational reasons in some arrangements.

In one implementation, each of the footwear interfaces 42 comprises Rexolite® available from C-LEC plastics, Inc. and has a thickness 25.5 mm. Rexolite® has extremely low loss at microwave frequencies, a relatively low dielectric constant of 2.53, and is mechanically stiff and strong. In one embodiment, the antenna arrays 20 are mounted underneath the footwear interfaces 42 with an air gap or clearance of 4.5 mm between the antenna arrays 20 and footwear interfaces 42.

The layer of material above the footwear interfaces 42 corresponding to footwear 43 is modeled as having a dielectric constant of 1.50. This value was determined empirically to work well for a range of different footwear. Accordingly, in some embodiments, the transmitted and received electromagnetic waves pass through different layers of media having different dielectric constants including the soles of the footwear 43, the footwear interface 42, and the abovementioned air gap between the antenna arrays 20 and the footwear interface 42.

Referring to FIGS. 5A and 5B, example scanning operations performed by footwear scanning system 14 are shown and described. During scanning of footwear of an individual, shuttle 44 makes one complete rotation beneath the base 16 of the footwear scanning system and the footwear 43.

Referring to FIG. 5A, each antenna array 20 includes a linear row of transmit antennas 60 and a linear row of receive antennas 62. Pairs of antennas are selected each including one transmit antenna and one receive antenna during scanning of the footwear. In one embodiment, transmit and receive antennas 60, 62 are circularly polarized (CP) spiral antennas designed for wide-beamwidth and wide bandwidth performance over a full 10-40 GHz range. Direct reflections reverse the handedness of circularly polarized waves, so the receive 62 antennas are designed with opposite handedness, or crossed polarization. Further details regarding use of a 10-40 GHz frequency range and incorporation of wide beamwidth circularly polarized antennas for scanning operations are discussed in J. L. Fernandes, J. R. Tedeschi, D. M. Sheen, and D. L. McMakin, "*Three-dimensional millimeter-wave imaging for concealed threat detection in shoes*," presented at the SPIE Defense, Security, and Sensing Conference, Baltimore, Md., USA, 2013; and D. M. Sheen et al., "*Wide-bandwidth, wide-beamwidth, high-resolution, millimeter-wave imaging for concealed weapon detection*," presented at the SPIE Defense, Security, and Sensing, Baltimore, Md., USA, 2013, the teachings of each of which are incorporated herein by reference.

Referring to FIG. 5B, the antenna arrays 20 may be radially offset with respect to one another to provide interlacing of data samples from both arrays 20, and an increased number of sampling points compared with arrangements where the arrays 20 are not radially offset in one embodiment. The arrays 20 are offset with respect to one another by a distance equal to D/4 in one implementation. Antennas of the first antenna array 20 define a plurality of sampling points at different radial locations from the axis of rotation of the shuttle 44 compared with the sampling points defined by the antennas of the second antenna array 20.

For example, the leftmost transmit antenna 60 and the leftmost receive antenna 62 of the illustrated array 20 are selected at a moment in time with a respective virtual sampling point 64 being defined at the midpoint between the selected pair of antennas 60, 62. The sampling point 64 of these selected antennas 60, 62 occurs along arc 65 during sampling operations and rotation of the shuttle. The pair of antennas including the innermost transmit antenna 60 and the innermost receive antenna 62 of the antenna array not shown in FIG. 5B define midpoints along arc 66 which is adjacent to the arc 65 providing increased resolution compared to arrangements wherein the antenna arrays 20 are not offset. In particular, a two-row antenna array of N antennas without interlacing achieves N–1 radial samples while a two-row antenna array of N antennas with interlacing achieves 2(N–1) radial samples. This embodiment enables high-resolution imaging using a reduced number of antennas.

In addition, the use of antenna array 20 having two rows of antennas allows fabrication of the arrays with integrated switches and without complex signal routing. The antenna arrays 20 may be fabricated upon respective printed circuit boards which also include surface mount technology (SMT) switches for antenna switching and selection of antenna pairs during scanning operations. In one embodiment, signal distribution is routed with transmission distribution on one side of the printed circuit board of a given antenna array 20 and receive distribution on the other side. The illustrated arrangement of antenna arrays 20 also allows greater spacing between physical antennas while preserving fine subwavelength sampling of the aperture in some embodiments.

Conventional imaging methods previously developed for body scanning are based on a uniform medium assumption and uniform aperture sampling. However, the use of the footwear interfaces 42 to support the footwear 43 and protect the antenna arrays 20 violates the uniform medium approximation. Additionally, an air gap between the antenna array 20 and the respective footwear interface 42 further complicates the imaging scenario. Conventional imaging methods yield unacceptable results due to the presence of a heterogeneous, layered medium.

In one embodiment, processing circuitry 29 performs an image reconstruction method described below that is based on backprojection coupled with raytracing through a layered media model of the propagation path for optimal imaging performance. Processing circuitry 29 of host computer 30 is configured to process output of transceiver 24 corresponding to the received electromagnetic waves reflected from the footwear 43 to perform the image reconstruction in one embodiment.

Figure 6:
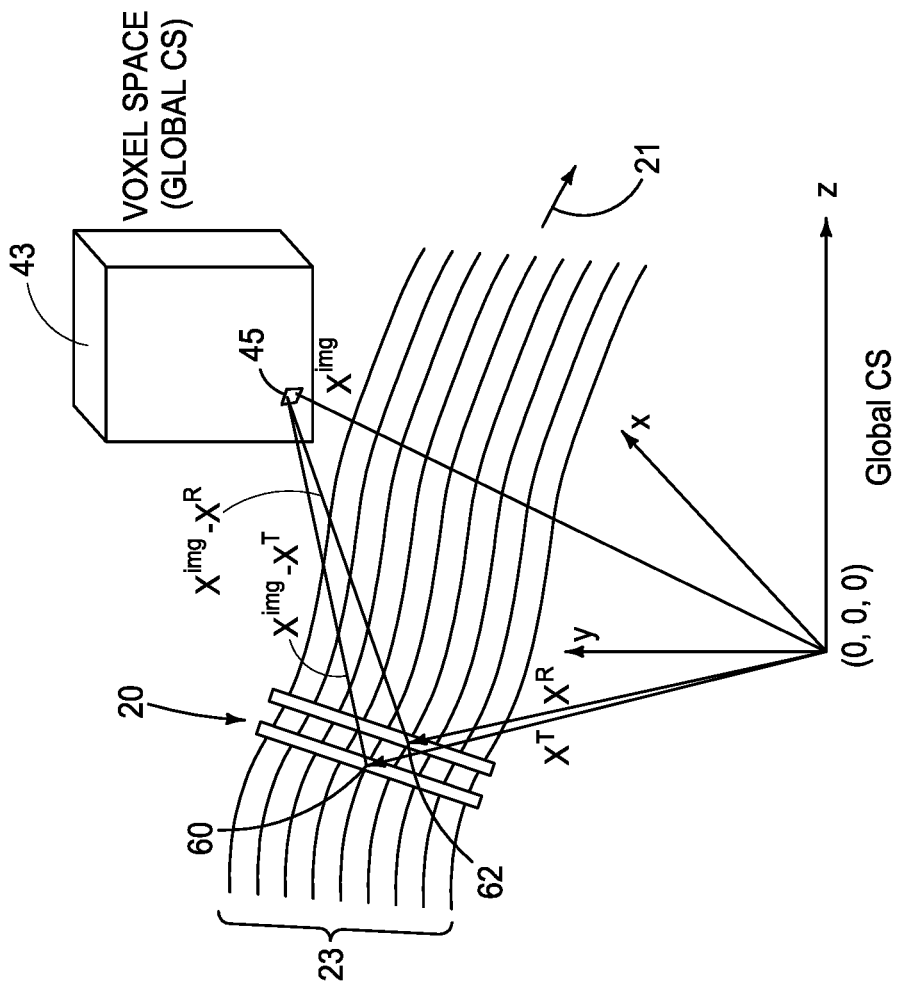
FIG. 6 is an illustrative representation of scanning operations with respect to a stationary target according to one embodiment.

Referring to FIG. 6, an example implementation of multistatic scanned aperture imaging is shown where antenna array 20 is moved with respect to a stationary target, such as footwear 43 being supported by a footwear interface. Active 3D radar imaging utilizes effective formation of a two-dimensional spatial aperture 23 by moving antenna array 20 in a scan direction 21 that enables lateral resolution, and a wide frequency bandwidth that enables depth resolution. In one straightforward configuration, a compact transceiver (T/R) is raster-scanned over a 2D spatial aperture 23.

At each sampled position on the aperture 23 a selected transmit antenna 60 emits a diverging (wide beamwidth) wave, which interacts with, and is scattered by, the imaging target or footwear 43. The scattered wave front is then sampled by a selected receive antenna 62. The signal is obtained over a wide frequency bandwidth by using a swept frequency source or using a temporally short impulse source. Wide-angle illumination of the target over a large spatial aperture provides lateral resolution. The radar data collected by the active system are three-dimensional (two spatial dimensions and one frequency dimension) and are completely unfocused as collected by the system. An image reconstruction algorithm is discussed below according to one embodiment to mathematically focus the image in all three spatial dimensions. High-resolution 3D imaging is optimized using large apertures with targets at close range, i.e. in the near-field of the aperture.

In the embodiments discussed above, the axes of the linear antenna arrays 20 are radially oriented with respect to the rotating shuttle that scans the array over a circular 2D spatial aperture. For mathematical analysis, this 3D imaging configuration can be generalized as shown in FIG. 6 although the direction of movement of the antenna array and the scanned aperture 23 would be circular.

Versatile image reconstruction can be performed using a process called backprojection that is tailored for each specific imaging configuration. A generalized focused imaging approach is discussed in D. Mensa, *High Resolution Radar Cross Section Imaging*, Norwood, Mass., Artech House, 1991. This approach is based on the supposition that the imaging algorithm for any form of frequency and spatial diversity is eminently simple: the image is formed by the integrated product of the measured data multiplied by the conjugate phase history (i.e., radar imaging data) postulated for a point located at each pixel in the image space This approach is intuitive, because if there is scattering from a given voxel location, then a component of the phase-history signal will be multiplied by its exact conjugate phase and will integrate in-phase to yield a strong image intensity at that voxel location. The response from scattering at other positions will add out-of-phase and not contribute significantly to the image intensity at that location. This style of image reconstruction is referred to as backprojection and can be adapted to focus images from non-uniform apertures of essentially any configuration. The method is straightforward to implement, however, the principal drawback of this generalized approach has been its computational inefficiency compared to other methods, such as FFT-based methods. This limitation is less important with recent availability of extremely high-performance multicore CPUs and GPUs that are well-suited to this approach.

One embodiment of processing the radar data by the processing circuitry 29 to generate images assumes a uniform propagation medium with modifications to compensate for the heterogeneous, layered medium of the footwear scanning system. Additional details of image generation in the presence of a uniform propagation medium are set forth in D. Sheen, D. McMakin, and T. Hall, "*Near-field three-dimensional radar imaging techniques and applications*," Appl. Opt., vol. 49, no. 19, p. E83, July 2010; and D. M. Sheen, D. L. McMakin, and T. E. Hall, "*Three-Dimensional Millimeter-Wave Imaging for Concealed Weapon Detection*," IEEE Trans. Microw. Theory Tech., vol. 49, no. 9, 2001, the teachings of each of which are incorporated herein by reference.

The antenna array 20 is a multistatic linear array configuration that uses combinations of transmit (T) and receive (R) antennas to electronically scan an effective sample location (or phase center) along the axis of the array 20. Radar phase-history data are recorded coherently and can be represented by the 3D complex function (or discrete data set), $S(a_1,a_2,f)$ where $a_1$ and $a_2$ are the aperture axes and f is the frequency. In this case $a_1$ represents the scanned motion axis and $a_2$ represents the array axis. The generalized imaging approach suggested by Mensa can be implemented by $$v(x^{img}) = \sum_{motion, a_1} \sum_{array, a_2} w(a_1, a_2, f) \sum_f S(a_1, a_2, f) e^{j2kr} \quad \text{Equation 1}$$

where $v(x^{img})$ is the complex image amplitude at voxel location $x^{img}$, $k=2\pi f/c$ is the wavenumber at the frequency (f), c is the speed of light, and an aperture weighting term $w(a_1,a_2,f)$ is introduced to provide amplitude weighting to reduce side lobes or other artifacts in the image. The approach is made significantly more efficient by converting from the frequency domain to the range domain using the inverse Fast Fourier Transform (iFFT) using $$v(x^{img}) = \sum_{motion, a_1} \sum_{array, a_2} w(a_1, a_2, f) s(a_1, a_2, r) e^{j2k_c r} \quad \text{Equation 2}$$

where $k_c=2\pi f_c/c$ is the wavenumber at the center frequency $(f_c)$ and $$s(a_1,a_2,r) = \{iFFT(w(f)S(a_1,a_2,f))e^{j2k_1 r_n}e^{-2k_c r_n}\}|_r \quad \text{Equation 3}$$

is the range-domain equivalent of the input data interpolated onto a range of r values. In this expression, $r_n$ are the available range samples after the iFFT and $k_1$ is the wavenumber at the starting frequency. The phase factors $e^{j2k_1 r_n}e^{-j2k_c r_n}$ correct the phase of the range-domain waveforms and remove the fast phase variation to allow for accurate interpolation. The weighting factor in this case has been separated into a frequency weighting, w(f), and an aperture weighting, $w(a_1,a_2)$. The range, r, is one-half the round-trip distance from the selected transmit antenna 60 to the target voxel 45 of the image volume and back to the selected receive antenna, or $$r = (|x^{img} - x^T| + |x^{img} - x^R|)/2 \quad \text{Equation 4}$$

where $x^T$ and $x^R$ are the positions of the transmit and receive antennas 60, 62, respectively.

Evaluation of equations (2) using (3) and (4) over a full 3D grid of target voxels $x^{img}$ completes the image reconstruction. The use of the FFT to convert the radar data to the range domain reduces the computational burden to $O(N^5)$ (where N represents the size of each data and image dimension) for a substantial increase in efficiency and image reconstruction speed and compared with a computational burden of $O(N^6)$ if equation (1) is used.

The aperture-weighting term used in the image reconstruction formulas, $w(a_1,a_2)$, can be used to control side lobes in the scanned microwave- or mm-wave synthetic aperture radar imaging systems disclosed herein. For scanned apertures, a Hamming, Hanning, Kaiser, or other window function may be applied to each aperture dimension of the data to control side lobes. Windowing the data along the frequency axis is also used to control side lobes in the range direction.

In one embodiment, the footwear scanning system 14 is configured such that the bottom of an image volume including plural voxels corresponds to the surface of the footwear interface 42 that supports the footwear 43 (or slightly below) and the lateral dimensions of the image volume extend upwardly from the footwear interfaces 42 to a vertical height of approximately 20 cm.

Figure 7:
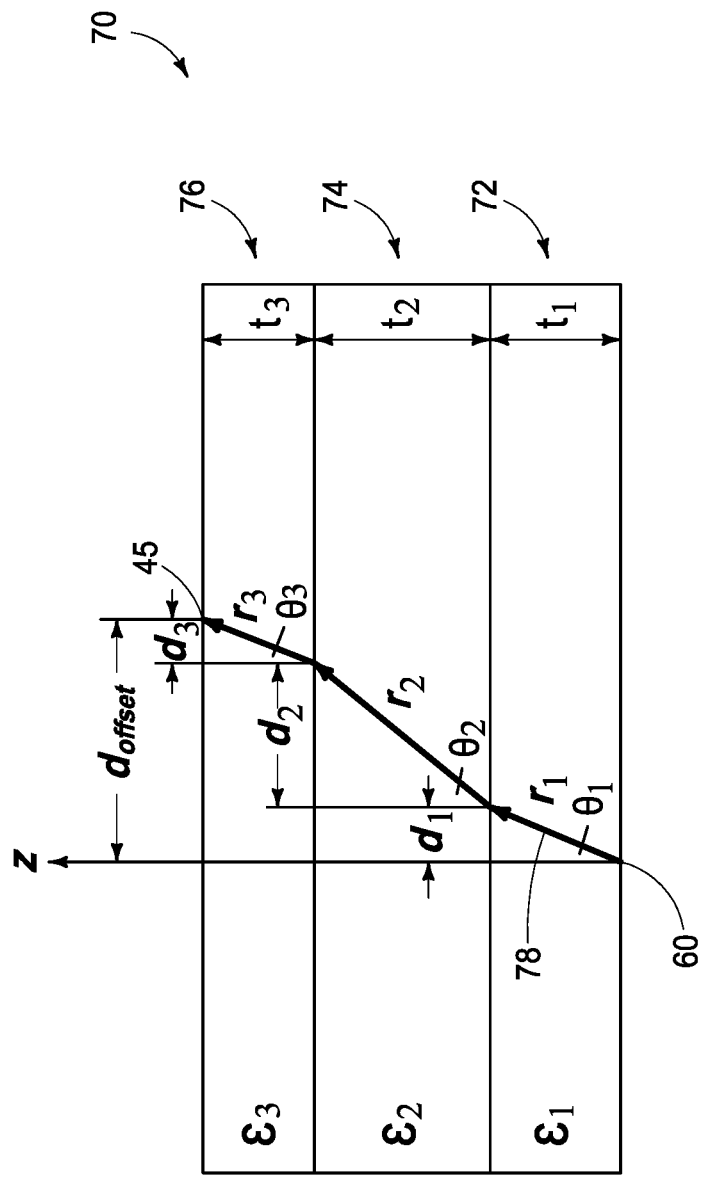
FIG. 7 is a cross-sectional view of propagation of an electromagnetic wave through a heterogenous medium according to one embodiment.

The image reconstruction process detailed above assumes that the medium is uniform. However, as discussed above, a footwear scanning is non-uniform but can be accurately modeled as a layered medium 70, as shown in FIG. 7. The layered medium 70 includes layers of different materials having different dielectric constants and include an air gap 72, material of the footwear interface 74 and material of the sole of the footwear 76.

The generalized imaging method described above utilizes the round-trip phase shift of a wave emitted by the transmitter reflected by contents within the footwear and returned to the receiver. In a uniform medium, this is captured by the $e^{j2kr}$ term in Equation 1, where the effective radar range is given by Equation 4. For a layered medium 70 as is present with arrangements that scan footwear being worn by an individual, the above-described imaging algorithm can be utilized if the round-trip phase shift can be determined that accounts for the velocity of propagation and path through the non-uniform, layered medium 70.

According to some embodiments discussed below, the processing circuitry 29 is configured to determine a phase shift of each of the transmitted and received electromagnetic waves and to use the phase shifts to modify intensities of the received electromagnetic waves to generate information, such as images, regarding the contents within the footwear 43. As discussed below, the processing circuitry 29 is configured to use a plurality of different dielectric constants corresponding to the different layers of media 70 to determine the phase shifts of the electromagnetic waves according to some embodiments. In one implementation discussed below, the processing circuitry is configured to determine an optical path length of each of the transmitted and received electromagnetic waves and to use the optical path lengths to determine respective ones of the phase shifts.

In one embodiment, round-trip phase shifts of electromagnetic waves between the transmission and reception of the electromagnetic waves through the layered (i.e., non-uniform) medium 70 can be determined using a ray tracing procedure as shown in FIG. 7 in one embodiment. The reflections may be tailored to appear at ranges distinct from the soles of the footwear 43 with use of a relatively thick footwear interface. Additionally, the imaging process will tend to defocus those responses.

The ray tracing starts with an electromagnetic wave 78 emanating from a transmit antenna 60 at a known angle and propagates through the medium 70 following Snell's law of refraction at each interface. Angles $\theta_i$ are determined using Snell's law of refraction, $\sin \theta_i = \sqrt{\varepsilon_i/\varepsilon_{i-1}} \sin \theta_{i-1}$ where $\theta_1$ is the initial (assumed known) angle, $\varepsilon_i$ is the dielectric constant in layer i. Ray offsets $d_i$ and path lengths $r_i$ are determined from the layer thicknesses $t_i$ and angles $\theta_i$ as $$d_i = t_i \sqrt{\frac{\sin^2 \theta_i}{1 - \sin^2 \theta_i}}$$

$$r_i = t_i \sqrt{\frac{1}{1 - \sin^2 \theta_i}}$$

Equation 5

The one-way phase-shift through this layered medium is determined by the wavenumber multiplied by the optical path length (OPL) defined as $$OPL = \sum_{i=1}^{n_{regions}} r_i \sqrt{\varepsilon_i}$$

Equation 6 where $n_{regions}$ is the number of layers traversed. The principal drawback to the above ray tracing approach is that we wish to calculate the OPL from the transmit antenna with known position to each (also known) voxel location 45. The initial angle that corresponds to this ray path cannot be calculated directly but would need to be calculated iteratively. This would be highly inefficient as this iterative calculation would be in the inner loop of an $O(N^5)$ calculation in Eqn. 2.

One embodiment of the disclosure provides an alternative procedure including pre-computing the ray-tracing results and storing them in a database, such as look-up tables (LUTs), that can be used to extract the necessary optical path length for each given voxel location corresponding to a location of the antenna array 20. In one embodiment, the locations of the transmit and receive antennas are known and correspond to respective voxel locations in an image volume. The locations of the transmit and receive antennas may be used to address the LUTs and the optical path lengths for the respective voxels of the image volume that correspond to the locations of the transmit and receive antennas are outputted by the LUTs. The optical path lengths are and used to focus the radar data as discussed further below.

Referring to FIG. 7, the origin can be assumed to coincide with each transmit or receive location and there is cylindrical symmetry around the z-axis, so two-dimensional LUTs may be used, i.e. a function of $(d_{offset}, z)$, which are the horizontal and vertical distances from the transmit 60 (or receive) antenna to the voxel location 45 and are known at the start of the imaging process. Note, that the ray that is reflected from the voxel location 45 can be traced back to the receive antenna by invoking reciprocity and tracing the ray from the receive location to the voxel 45 using the process outlined above. Accordingly, a single LUT may be used twice for the different locations of the transmit and receive antennas to determine the total range or phase delay due to the round-trip from the transmit antenna to the voxel and back to the receive antenna (the lateral offset is usually different for the transmit and receive antennas).

In one embodiment, the LUTs can be calculated by defining a uniform range of incident angles $\theta_{inc}$ and vertical positions z and calculating the offset for each position using equation 5 and saving the results of the calculations in a LUT $d_{offset,LUT}(\theta_{inc}, z)$.

Figure 8:
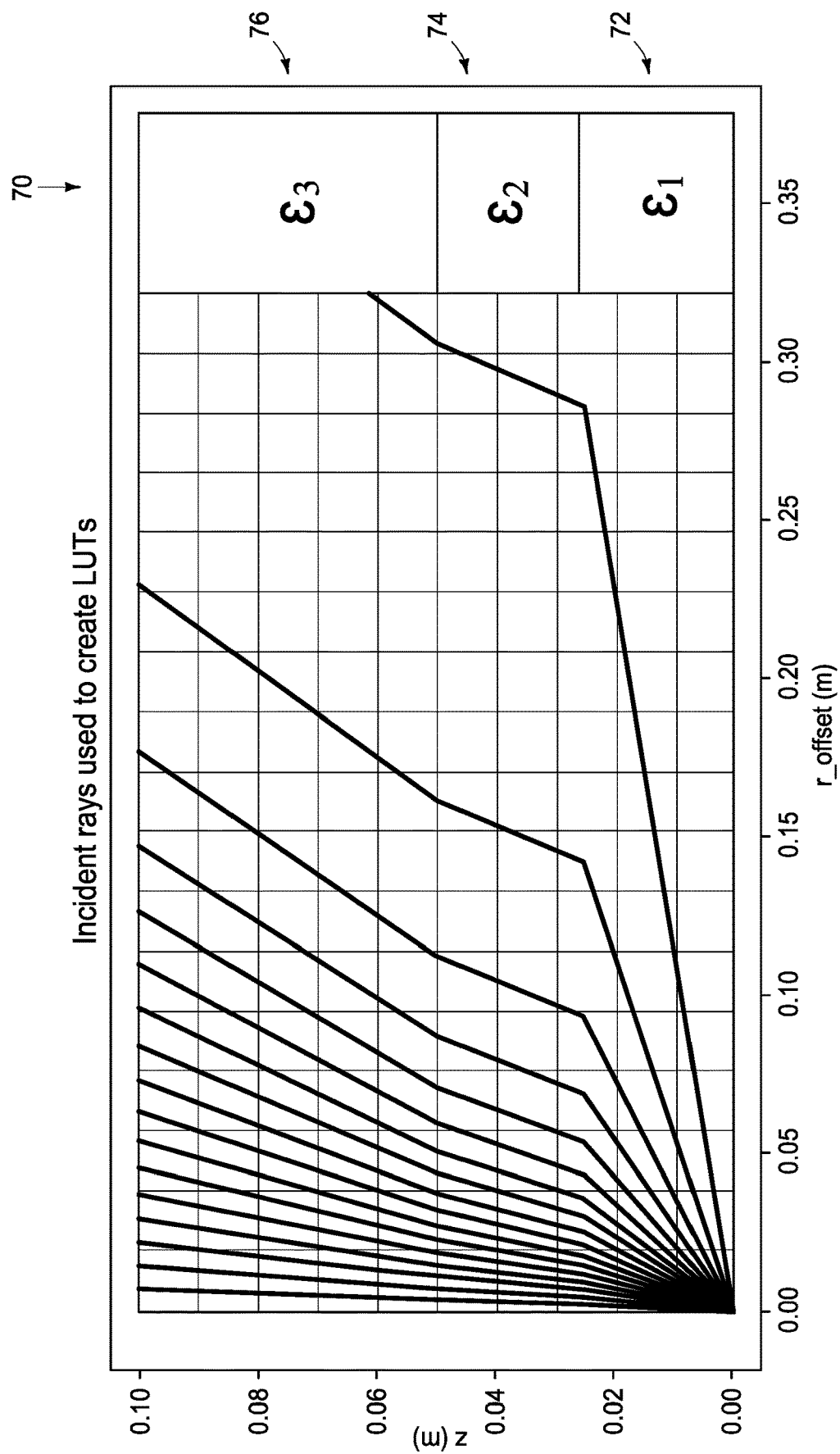
FIG. 8 is a graphical representation of incident rays propagating through a heterogenous medium according to one embodiment.

An example of this LUT calculation is shown in FIG. 8 including ray tracing through layered medium 70 to generate the optical path length LUT. This LUT can be inverted using linear interpolation to solve for the incident angle as a function of offset and vertical position. These results are then saved in a second LUT for the incident angle $\theta_{inc,LUT}$ $(d_{offset}, z)$. The incident angle LUT can then be used to create the desired LUT for optical path length (OPL) from the antenna location 60 to the voxel 45 as, $$OPL(d_{offset}, z) =$$

Equation 7

-continued $$\frac{h_1}{\sqrt{1-\sin^2\theta_1}}\sqrt{\varepsilon_1} + \frac{h_2}{\sqrt{1-\sin^2\theta_2}}\sqrt{\varepsilon_2} + \ldots \text{ where}$$

$$\theta_1 = \theta_{inc,LUT}(d_{offset}, z)$$

$$h_i = t_i \text{ if } z \text{ is above layer } i$$

$$h_i = z - \sum_{j=1}^{i-1} t_j \text{ if } z \text{ is inside layer } i \text{ (height within layer)}$$

$$\sin\theta_i = \sqrt{\frac{\varepsilon_{i-1}}{\varepsilon_i}} \sin\theta_{i-1} \text{ above layer 1}$$

The image reconstruction algorithm expressed in equation 2 can be modified to use this OPL LUT to calculate the effective range to the voxel 45, and is summarized as $$v(x^{img}) = \sum_{a_1, motion} \sum_{a_2, array} w(a_1, a_2) s(a_1, a_2, r_{eff}) \quad \text{Equation 8}$$

$$e^{j2k_c r_{eff}} \text{ focused image amplitude where}$$

$$x^{img} = (x_{img}, y_{img}, z_{img}) \text{ voxel position vector}$$

$$x^T = (x_T, y_T, z_T) \text{ } T \text{ antenna position vector}$$

$$x^R = (x_R, y_R, z_R) \text{ } R \text{ antenna position vector}$$

$$d_{offset,T} = \sqrt{(x_{img} - x_T)^2 + (y_{img} - y_T)^2}$$

$$d_{offset,R} = \sqrt{(x_{img} - x_R)^2 + (y_{img} - y_R)^2}$$

$$r_{eff} = (OPL(d_{offset,T}, z_{img} - z_T) + OPL(d_{offset,R}, z_{img} - z_R))/2$$

effective radar range

Figure 9:
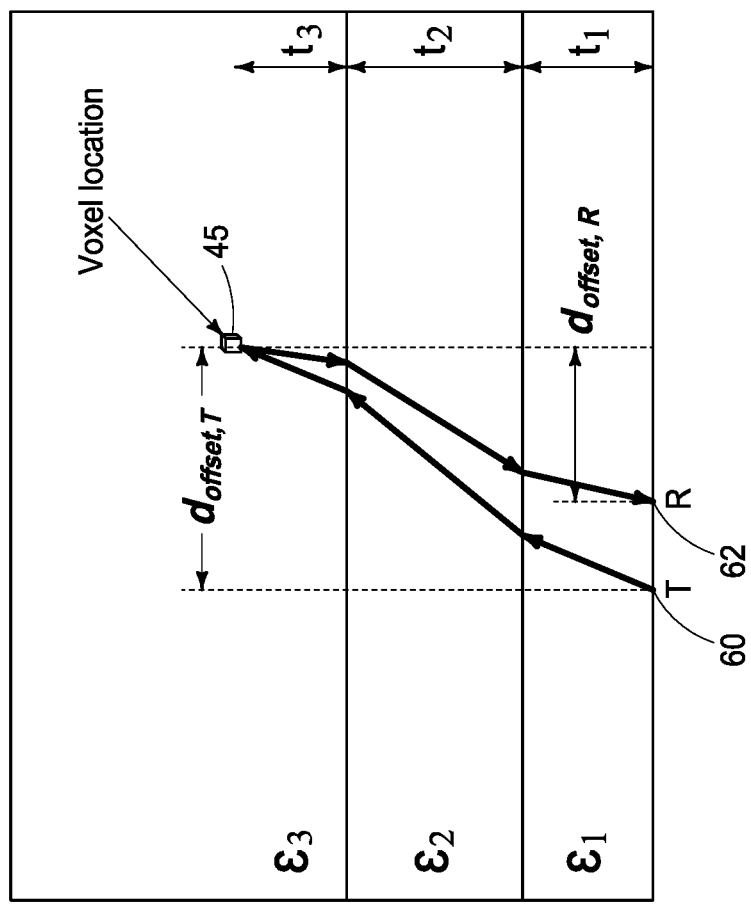
FIG. 9 is a graphical representation of determination of effective radar range from optical path lengths according to one embodiment.

This approach is shown graphically in FIG. 9. The values of $(d_{offset}, z)$ in this formula will not typically be sampled exactly in the optical path length LUT, however, accurate values may be easily and efficiently extracted using a bilinear interpolation process in one embodiment. The output of the LUT is the sum of the distance traveled in each layer multiplied by the square roots of the relative dielectric constants of the respective different layers which accounts for the slowing of the electromagnetic waves through layers of increased dielectric constants. In free space, the output of the OPL LUT is the distance between the transmit and receive antennas, but in a layered medium the output of the OPL LUT is the length of the ray in each layer multiplied by the square root of the respective layer.

According to the example embodiment discussed above, a plurality of optical path lengths between a plurality of antennas of the antenna array and voxels of an image volume about the footwear are stored in a database, such as a LUT. The processing circuitry is configured to address the database using a plurality of positions of the antennas during the transmission and reception of the electromagnetic waves to determine the optical path lengths of respective ones of the electromagnetic waves for use in determining phase shifts of the electromagnetic waves and images of the contents of the footwear.

Figure 10:
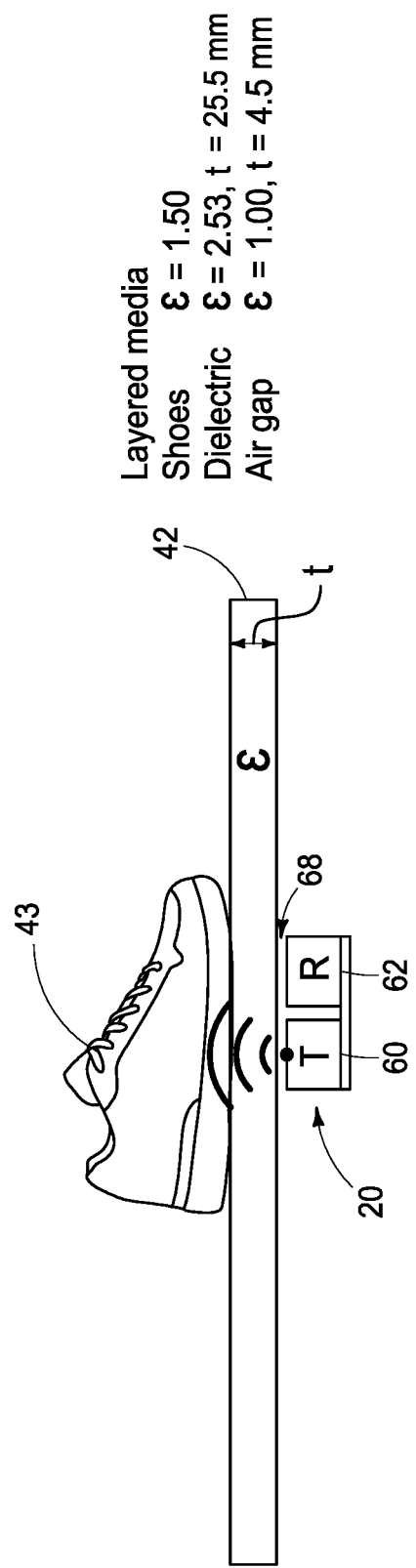
FIG. 10 is an illustrative representation of a footwear scanning system according to one embodiment.

Referring to FIG. 10, the footwear scanning system can be viewed in cross section with the transmit and receive antennas shown beneath the dielectric window. The scanner will then translate the antennas to complete the two-dimensional aperture shown in FIG. 5.

As discussed herein, example embodiments of the disclosure pertain to footwear scanning systems and methods. In some embodiments, the footwear scanning systems scan footwear of a person while the footwear is worn upon the person's feet. Scanning throughput of people is increased compared with other arrangements which require footwear to be removed. In addition, the footwear scanning systems may be used with body scanning systems enabling footwear and clothing to be scanned simultaneously according to some embodiments above.

Some embodiments of the disclosure are directed to footwear scanning systems that utilize at least one antenna array that is rotated in a circular path beneath the footwear interface configured to support the footwear and person being scanned. These footwear scanning systems may be utilized with existing cylindrical body scanning systems that are widely used. Scanning hardware of some footwear scanning systems discussed herein may have reduced height and have a circular envelope for direct integration into footbed form factors of existing cylindrical body scanners allowing the body and footwear of a person to be scanned at the same time without requiring divestment of the footwear and thereby increasing personnel scanning throughput. Furthermore, in some embodiments, the various components of the footwear scanning system may be shared with a corresponding body scanning system.

Some embodiments of the footwear scanning systems utilize millimeter-wave scanning to image footwear for anomalous materials or abnormal construction. Example prototypes discussed herein achieve high lateral and depth resolution with excellent performance observed for test targets and footwear scans.

Some embodiments of the disclosure utilize an image reconstruction algorithm that effectively focuses data from a multistatic array through layered media with only a minimal increase in computation burden compared to backprojection in a uniform propagation medium. In one embodiment, computation efficiency is obtained by pre-computing one or more look up tables that enable the optical path length (or effective radar range) from each transmit or receive antenna to be rapidly obtained. In addition, some image reconstruction methods described herein use positions of the antennas without requiring the data to be resampled to a uniform grid that can increase error. Some of the disclosed embodiments implement near-field operation wherein the antenna arrays are close to the imaging zone or volume.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended aspects appropriately interpreted in accordance with the doctrine of equivalents.

Further, aspects herein have been presented for guidance in construction and/or operation of illustrative embodiments of the disclosure. Applicant(s) hereof consider these described illustrative embodiments to also include, disclose and describe further inventive aspects in addition to those explicitly disclosed. For example, the additional inventive aspects may include less, more and/or alternative features than those described in the illustrative embodiments. In more specific examples, Applicants consider the disclosure to include, disclose and describe methods which include less, more and/or alternative steps than those methods explicitly disclosed as well as apparatus which includes less, more and/or alternative structure than the explicitly disclosed structure.

What is claimed is:

1. A footwear scanning system comprising:
   a base;
   a shuttle configured to rotate beneath the base;
   wherein the shuttle comprises an antenna array configured to transmit electromagnetic waves through the base into footwear above the base during the rotation of the shuttle and to receive electromagnetic waves reflected from the footwear during the rotation of the shuttle;
   a transceiver coupled with the antenna array and configured to apply electrical signals to the antenna array to generate the transmitted electromagnetic waves and to receive electrical signals from the antenna array corresponding to the received electromagnetic waves; and
   processing circuitry configured to process an output of the transceiver corresponding to the received electromagnetic waves to provide information regarding contents within the footwear.

2. The system of claim 1 wherein the transmitted and received electromagnetic waves pass through different layers of media having different dielectric constants.

3. The system of claim 1 wherein the processing circuitry is configured to determine a phase shift of each of the transmitted and received electromagnetic waves and to use the phase shifts to provide the information regarding the contents within the footwear.

4. The system of claim 3 wherein the transmitted and received electromagnetic waves pass through different layers of media, and the processing circuitry is configured to use a plurality of different dielectric constants corresponding to the different layers of media to determine the phase shifts of the received electromagnetic waves.

5. The system of claim 3 wherein the processing circuitry is configured to determine an optical path length of each of the transmitted and received electromagnetic waves and to use the optical path lengths to determine respective ones of the phase shifts.

6. The system of claim 5 wherein the transmitted and received electromagnetic waves pass through different layers of media having different dielectric constants, and the processing circuitry is configured to use the dielectric constants to determine the optical path length of each of the transmitted and received electromagnetic waves.

7. The system of claim 6 wherein the processing circuitry is configured to use the optical path lengths to determine effective ranges between antennas of the antenna array and voxels of the image volume and to use the effective ranges to process the output of the transceiver including adjusting intensities of the voxels of the image volume.

8. The system of claim 5 wherein a plurality of optical path lengths between a plurality of antennas of the antenna array and voxels of an image volume about the footwear are stored in a database, and wherein the processing circuitry is configured to address the database using a plurality of positions of the antennas during the transmission and reception of the electromagnetic waves to determine the optical path lengths of respective ones of the transmitted and received electromagnetic waves.

9. The system of claim 8 wherein a motor is configured to apply a force to the shuttle to rotate the shuttle about an axis, and wherein the motor is configured to generate information regarding the positions of the antennas.

10. The system of claim 1 wherein the base comprises a footwear interface configured to support the footwear and to pass the transmitted and received electromagnetic waves.

11. The system of claim 10 wherein the transmitted and received electromagnetic waves pass through soles of the footwear, the footwear interface, and an air gap between the antenna array and the footwear interface.

12. The system of claim 10 wherein the footwear interface has a dielectric constant of 4 or less.

13. The system of claim 1 wherein the antenna array is a first antenna array, and wherein the shuttle further comprises a second antenna array.

14. The system of claim 13 wherein the first and second antenna arrays are configured to transmit the electromagnetic waves towards the footwear from locations on opposite sides of an axis of rotation of the shuttle.

15. The system of claim 13 wherein a plurality of antennas of the first and second antenna arrays are radially offset with respect to one another, and the antennas of the first antenna array define a plurality of sampling points at different radial locations from the axis of rotation of the shuttle compared with the sampling points defined by the antennas of the second antenna array.

16. The system of claim 1 wherein the processing circuitry is configured to process an output of the transceiver to provide information regarding non-metallic contents within the footwear.

17. The system of claim 1 wherein the transmitted and received electromagnetic waves comprise a plurality of different frequencies of a frequency sweep.

18. The system of claim 17 wherein the transmitted and received electromagnetic waves are within a frequency range of 10-40 GHz.

19. The system of claim 1 wherein the antenna array comprises a plurality of antennas individually configured to one of transmit the electromagnetic waves or receive the received electromagnetic waves, and wherein the antennas are positioned at a plurality of different radial locations with respect to a center of rotation of the shuttle.

20. The system of claim 1 wherein the shuttle is configured to rotate in a plane that is substantially parallel with a planar surface of the base that supports the footwear.

21. The system of claim 1 wherein the shuttle is configured to transmit the electromagnetic waves into a substantially circular area of a planar surface of the base that supports the footwear.

22. The system of claim 1 wherein the shuttle is configured to rotate about an axis that is substantially perpendicular to a planar surface of the base that supports the footwear.

23. A footwear scanning system comprising:
   an antenna array comprising a plurality of antennas configured to transmit electromagnetic waves into footwear and to receive electromagnetic waves from the footwear;
   a transceiver coupled with the antenna array and configured to apply electrical signals to the antenna array to generate the transmitted electromagnetic waves and to receive electrical signals from the antenna array corresponding to the received electromagnetic waves;
   wherein the transmitted and received electromagnetic waves pass through different layers of media that have different dielectric constants; and
   processing circuitry coupled with the transceiver and configured to determine a phase shift of each of the transmitted and received electromagnetic waves and to use the phase shifts to provide information regarding contents within the footwear.

24. The system of claim 23 wherein the processing circuitry is configured to modify intensities of the received electrical signals using respective ones of the phase shifts.

25. The system of claim 23 wherein the processing circuitry is configured to use the different dielectric constants to determine the phase shifts of the transmitted and received electromagnetic waves.

26. The system of claim 23 wherein the processing circuitry is configured to determine an optical path length of each of the transmitted and received electromagnetic waves and to use the optical path lengths to determine the phase shifts.

27. The system of claim 23 wherein a plurality of optical path lengths between different positions of antennas of the antenna array and voxels of an image volume about the footwear are stored in a database, and wherein the processing circuitry is configured to address the database using a plurality of positions of the antennas during the transmission and reception of the electromagnetic waves to determine the optical path lengths of respective ones of the transmitted and received electromagnetic waves.

28. The system of claim 23 further comprising a shuttle comprising the antenna array, and wherein the shuttle and the antenna array are configured to rotate during the transmission and reception of the electromagnetic waves.

29. The system of claim 23 wherein the different layers of media are different layers of the footwear.

30. The system of claim 23 wherein the processing circuitry is configured to use phase of the received electromagnetic waves to provide the information regarding the contents within the footwear.

31. The system of claim 23 wherein the phase shift is a wave phase shift, and wherein the processing circuitry is configured to:
  determine a plurality of layer phase shifts for respective ones of the layers of media; and
  use the layer phase shifts to determine the wave phase shift.

* * * * *